United States Patent [19]
Sargent et al.

[11] Patent Number: 5,601,982
[45] Date of Patent: Feb. 11, 1997

[54] METHOD AND APPARATUS FOR DETERMINING THE SEQUENCE OF POLYNUCLEOTIDES

[76] Inventors: Jeannine P. Sargent, 22270 Kendle St., Cupertino, Calif. 95014; Jeff Marks, 4730 Cielo Vista Way, San Jose, Calif. 95129

[21] Appl. No.: 384,919

[22] Filed: Feb. 7, 1995

[51] Int. Cl.$^6$ .......................................... C12Q 1/68
[52] U.S. Cl. ................ 435/6; 435/287.2; 422/82.01; 422/82.05; 250/309; 250/311; 324/158.1
[58] Field of Search ................ 435/6, 287.2; 422/82.01, 422/82.05; 436/89; 250/309, 311, 442.11; 324/158.1

[56] References Cited

U.S. PATENT DOCUMENTS

| | | | |
|---|---|---|---|
| 5,106,729 | 4/1992 | Lindsay et al. | 435/6 |
| 5,242,974 | 9/1993 | Holmes | 525/54.1 |
| 5,252,743 | 10/1993 | Barret et al. | 548/303 |
| 5,270,214 | 12/1993 | Sessler et al. | 436/94 |
| 5,470,707 | 11/1995 | Sasaki et al. | 435/6 |

FOREIGN PATENT DOCUMENTS 5-244997  9/1993  Japan .............................. C12Q 1/68

OTHER PUBLICATIONS

Hunkapillar et al. (1991) Science 254:59–74.
Snow et al. (1993) *Appl Phys Lett* 63:749–751.
Weisenhorn et al. (1990) *Scanning Microsc.* 4:511.
M. Salmeron et al. (1990) *J. Vac. Sci. Tech.* 8:635.
Driscoll et al. (1990) *Nature* 346:294.
Allison et al. (1990) *Scanning Microsc.* 4:517.
Lindsay and Phillip (1991) *Genet. Anal. Tech. Appl.* 8:8.
*STM and SFM in Biology*, ed. O. Marti and M. Amrein, 1993, Academic Press pp. 229–257.
Huang et al. (1992) Anal. Chem. 64:2149–2154.
Lindsay et al. (1992) Biophys. J.61:1570–1584.
Lindsay et al. (1989) Science 244:1063.
Beebe et al. (1989) Science 243:370.
Dunlap et al. (1993) P.N.A.S. 90:7652–7655.
Allison et al. (1992) Ultramicroscopy 42–22:1088–1094.
Jing et al. (1993) P.N.A.S. 90:8934–8938.
Kabata et al. (1993) Science 262:15611563.
Lyubchenko et al. (1992) J. Mol. Struct. & Dyn. 10:589–606.
Innis et al. (1988) P.N.A.S. 85:9436–9440.

*Primary Examiner*—David A. Redding
*Attorney, Agent, or Firm*—Flehr, Hohbach, Test, Albritton & Herbert

[57] ABSTRACT

Methods for determining the sequence of a polynucleotide are described. The method utilizes a novel apparatus. Linearly oriented nucleic acids are scanned by scanning tunneling microscopy, and the presence of base specific labels determined. The information is compiled for different labels, and the data sets combined to provide the full nucleotide sequence.

16 Claims, 7 Drawing Sheets

GGGGGAATTCCGTCAGACTAAC

```
-----AA---------A-A---AA-
GGGGG-------G---G-G-----
------TT----T-------T---
---------CCC--C-----C---C
```

*Figure 4C*

GGGGGAATTCCGTCAGAGCTAAC

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

G T A T C A C A C G A G G C C C T T     18

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:2:

A T G C G T C C G G C G T A G A     16

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:3:

A G C G G C C G C T C G C C A G G G T T T T C C C A G T C A C G A C     34

METHOD AND APPARATUS FOR DETERMINING THE SEQUENCE OF POLYNUCLEOTIDES

TECHNICAL FIELD

The field of this invention is the sequencing of nucleic acids through the use of microfabricated substrates and scanning tunneling microscopy.

BACKGROUND

A commitment has been made in recent years by several governments to support the sequencing of the entire human genome. The human genome contains roughly three billion base pairs of DNA, and consequently the project has generated immense interest in large-scale DNA sequencing. Even after the complete human genome has been sequenced, the determination of individual genotypes in clinical screening remains an important consideration for DNA sequencing. Genotyping performed using techniques such as Southern blotting will suffer from imprecision, and even at best cannot provide detailed sequence information. A simplified method for rapid DNA sequencing would allow routine clinical determination of medically important genes.

Traditional methods for obtaining a DNA sequence all share a fundamental approach. A DNA species is isolated, and a complete nested set of DNA fragments is generated, each fragment having a common starting point and being one base longer than the preceding fragment. The set of fragments is commonly produced by either limited chemical cleavage (Maxam and Gilbert method), or enzymatically, by DNA synthesis in the presence of a small amount of a chain terminating nucleotide (Sanger method). Both methods utilize recognition of the specific bases that comprise DNA to generate sets of fragments, each corresponding to termination at a single base species.

The nested fragments are then size fractionated to determine the order of bases. Polyacrylamide gel electrophoresis has been the method of choice for a number of years, however it suffers from limitations in the length of fragments that can be resolved, and in the length of time required for good separation. In order to determine the nucleotide sequence, the fragments must be labeled with a detectable label, such as a radioisotope or fluorochrome. The label is used to visualize the separation pattern.

The length of sequence data available from a single reaction set as described above is limited to perhaps one thousand bases. The reactions and separations are time-consuming, expensive, and require a skilled technician. Resolution by gel electrophoresis may lead to inaccuracies, and limit the length of sequence which is obtained from a given set of reactions. It is therefore of interest to devise means by which DNA sequencing can be simplified, particularly utilizing methods which lend themselves to automation.

RELEVANT LITERATURE

A review of current methods used in large scale and automated DNA sequencing may be found in Hunkapillar et al. (1991) *Science* 254:59–74.

An overview of the use of scanning tunneling microscopy with biological molecules may be found in *STM and SFM in Biology*, ed. O. Marti and M. Amrein, 1993, Academic Press. The use of STM to visualize DNA is described in Lindsay and Phillip (1991) *Genet. Anal. Tech. Appl.* 8:8; Allison et al. (1990) *Scanning Microsc.* 4:517; Driscoll et al. (1990) *Nature* 346:294; M. Salmeron et al. (1990) *J. Vac. Sci. Tech.* 8:635. The use of AFM to visualize DNA is described in Weisenhorn et al. (1990) *Scanning Microsc.* 4:511.

The use of STM in microfabrication is discussed in Snow et al. (1993) *Appl Phys Lett* 63:749–751.

BRIEF DESCRIPTION OF THE DRAWINGS

The invention will be more fully understood from the following description, read in connection with the accompanying drawings, of which.

SUMMARY OF THE INVENTION

Apparatuses and methods are provided for determining the sequence of nucleotides in a nucleic acid, i.e. DNA or RNA. The molecule, modified with a base specific label by analog incorporation during synthesis or by complementation, is linearly oriented on a planar surface, and the position of each labeled base is determined by scanning the length of the molecule with scanning microscopy. The process is repeated for each of the four bases, and the data sets combined to provide the full nucleotide sequence. The process is useful for determining any DNA sequence, i.e. chromosomal DNA, DNA episomes, fragments and oligonucleotides, RNA, etc.

The apparatus includes fabricated substrates having an alignment path for nucleic acid sequencing. Such substrates can have a plurality of alignment paths to facilitate multiple molecule scanning. The alignment paths have a binding surface to which nucleic acids adhere. A system is provided for use in determining the sequence of nucleic acids; having a scanning microscope, fabricated substrate, and data analysis computer.

Methods for determining the sequence of a nucleic acid using fabricated substrates and scanning microscopy are provided. Methods for the preparation, labeling and alignment of nucleic acids are also provided.

DESCRIPTION OF THE SPECIFIC EMBODIMENTS

Methods and apparatuses are provided for determining the sequence of bases in a nucleic acid molecule. The nucleotide sequence is determined by orienting single-stranded nucleic acid molecules on a surface having one or more linear alignment paths, and determining the presence of base specific labels along the length of the molecule by scanning microscopy. The process is repeated with labels specific for each base, and the data sets thus provided are combined to give the complete nucleotide sequence.

Nucleic acids are polymers having a phosphate backbone, attached to which are sugars and heterocyclic nitrogenous bases. Naturally occurring nucleic acids are synthesized from nucleotide triphosphates comprising a combination of four species of bases, purines: adenine (A) and guanosine (G), and pyrimidines: cytosine (C) and one of thymidine (T) or uracil (U). A nucleic acid can be chemically or enzymatically modified so that one of the four base species is labeled. Such a modification may be the result of synthesizing the molecule from a nucleotide triphosphate pool where one of the naturally occurring base species is substituted with an analog. Alternatively, the complementary binding specificity of the bases can be exploited, where a nucleotide or analog is added post-synthetically which will base pair with only one of the bases.

Figure 2A:
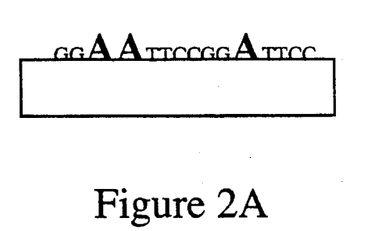
FIG. 2A is a longtitudinal view of a trench substrate, including DNA.
Figure 2B:
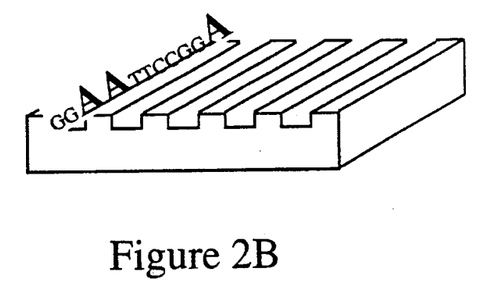
FIG. 2B is a cross-section of a trench substrate.
Figure 3A:
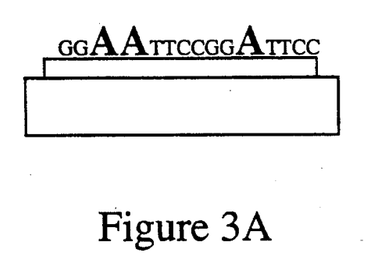
FIG. 3A is a longtitudinal view of a raised path substrate, including DNA.
Figure 3B:
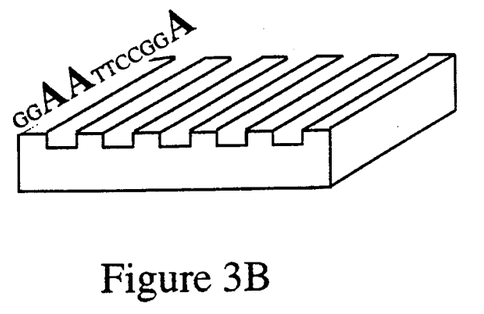
FIG. 3B is a cross-section of a raised path substrate.

In the subject method, a nucleic acid molecule is isolated and adhered through its phosphate backbone to the alignment path of a fabricated substrate 11, as shown in FIGS. 2 and 3. A base specific label alters the selected base and causes it to be distinguishable from the adjacent bases by scanning microscopy. The label may be differentiated by size or conductivity. For conductivity, a label comprising a single metal atom is generally sufficient for detection. For topographic detection, a label consisting of a group of at least about 10 Å, preferably at least about 15 Å in size, is sufficient for detection. The nucleic acid will generally also contain an initiation marker distinguishable by scanning microscopy, providing a reference for data analysis.

Analogs of bases with various groups are useful as a base specific label, e.g. biotin, FITC, coumarin, digoxigenin, hydroquinone/quinone, etc. covalently attached to the base through a linking group, as known in the art. Other labels of interest include complexed metals, i.e. metallocenes, e.g. ferrocene, dibenzenechromium, uranocene, bis(pentalenylnickel), etc. attached to the base through any convenient covalent linkage, as known in the art. It is preferable to use a linking group which is less than 5 Å in length, such that the label will be situated over a single base.

The substrate is then positioned for analysis of the nucleic acid by a scanning microscope. The scanning microscope may be scanning tunneling (STM) or scanning force (SFM), collectively, (SXM). For most purposes, STM will be used, because of its superior resolution. The microscope will have at least one probe, which will scan along the alignment path. The substrate may be analyzed in a wet cell, a controlled humidity cell, or a dry cell. A wet cell may further include a power source for generating electric potential, when used with a conductive binding surface as described below.

The substrate will be formed from a base comprising a material amenable to microfabrication, e.g. crystalline silicon; germanium; III–V compounds, e.g. indium antimonide, cadmium telluride, silver iodide, gallium arsenide, etc. The binding surface will usually be physically smooth, i.e. a scanning microscope will distinguish between the topography of a nucleic acid and the binding surface. Generally the base material will have a root mean surface number (RMS no.) of less than about 25% of the height of a DNA molecule, usually less than about 5 angstroms. Silicon is a convenient and inexpensive base material.

The substrate will comprise one or more alignment paths having a nucleic acid binding surface. The alignment paths may be of several different structures and there may be one or a plurality of paths. The substrate may vary in size, and will usually be large enough for convenient handling, at least about 100 mm on a side, and not more than about 10 cm on a side. The paths will usually be spaced at least about 1000 Å apart and not more than about 10,000 Å apart. The substrate size and spacing allows a very large number of paths to be fabricated relative to the number of molecules that will be scanned. Therefore, the number of paths may be any convenient number. Generally, the number of paths, multiplied by the binding efficiency of DNA on the paths, will provide aligned molecules in excess of the number that will be scanned. Generally the number of paths will be at least about 100 paths, more usually at least about 1000 paths, and may be as many as $10^6$ paths.

In one preferred embodiment, FIGS. 2A, 2B, the alignment path will be one or more trenches which are at least about 20 Å and not more than about 50 Å wide. The trenches will at least be about 5 Å and not more than about 50 Å deep, and will be at least about 1 μm, usually at least about 10 μm long, and may be about 100 μm or longer. The nucleic acid binding surface 7 will be at the bottom of the trench and may be an oxide surface covered with a film of highly polarized binding material, such as 3-aminopropyltriethoxysilane; or a conductive metal coating, e.g. an inert noble metal, such as gold, platinum, palladium, etc. Alternatively, the alignment path may comprise a path 8, either level with the surface of the substrate or, optionally, raised above the surface. The path will be sufficiently wide to bind the phosphate backbone of a nucleic acid, generally being at least about the width of the phosphate backbone. Usually the path will be at least about 5 Å and not more than about 50 Å wide. The height of the path may vary from a level surface to about 50 Å high, with the binding surface 9 at the top of the path. A substrate with a conductive surface will usually be employed in a wet cell, while the polar surface may be employed with either wet or dry cells.

The substrate with the aligned nucleic acid molecule(s) is placed in a scanning tunneling or atomic force microscope and the paths are scanned. The scanning may be sequential by a single tip or parallel with multiple tips. Scanning tunneling and force microscopes are well known and commercially available. Tunneling and atomic force microscopy for the surface characterization of molecules is described in Magonov (1993) *Applied Spectroscopy Reviews* 28:1–121.

Figure 1:
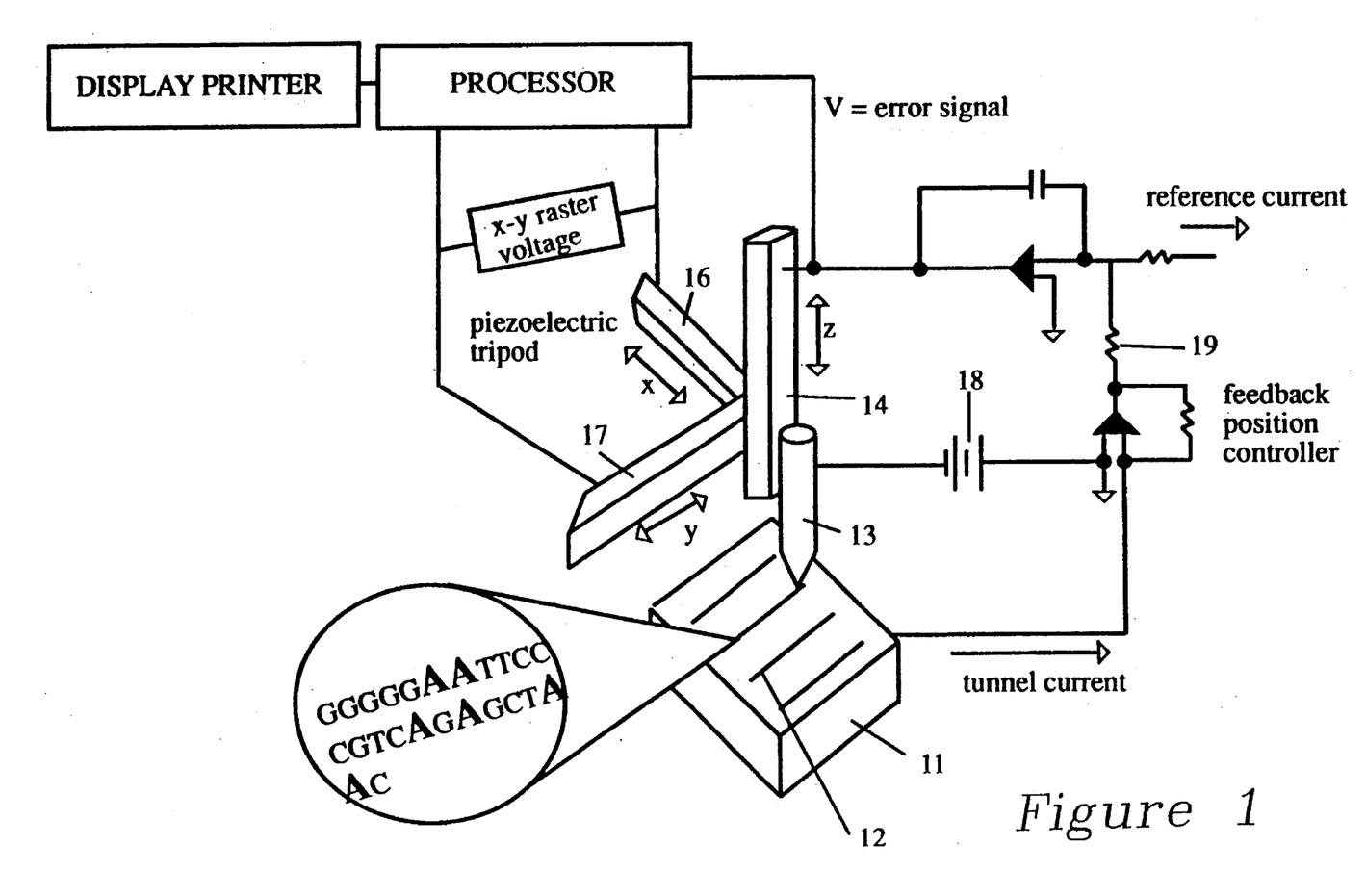
FIG. 1 is a diagram of the sequencing apparatus.

Turning now to FIG. 1, the substrate 11 with the aligned nucleic acid molecule(s) is placed in the microscope and paths 12 are scanned. The scanning may be sequential or simultaneous, if multiple tips (not shown) are used. The scanning tunneling microscope includes a fine metal tip 13, which may be tungsten, Pt-Ir, Pt-Rh, pure Pt, Au, and the like. For use in a wet cell the tip will be insulated, with glass, silicon, wax, etc. The tip is brought to within a few tenths of a nanometer of the surface of the molecule. This is accomplished with piezoelectric transducers arranged to form an orthogonal coordinate system: one transducer 14 is used to move the tip toward and away from the sample, and the other two 16, 17 are used to translate the tip laterally over the sample surface. A small bias voltage 18 ranging from a few millivolts to a few volts is applied across the gap between the tip and the sample. The tip is brought up to the sample until a small current begins to flow, typically in the order of a nanoampere. In a wet cell, it is desirable to keep the current below about 0.4 nA, for optimum resolution. A feedback loop 19 is then employed to measure the tunneling current compared with a fixed reference value. The tip is moved to maintain a constant current. Since the tunneling current varies by about a factor of 10 for every 0.1 nanometer change in spacing between the tip and the sample, the scanning tunneling microscope can resolve height differences of less than 0.01 nanometers. It has a lateral resolution of about 0.2 nanometers, roughly corresponding to the size scale of the atoms comprising the tip and the sample.

Figure 4A:
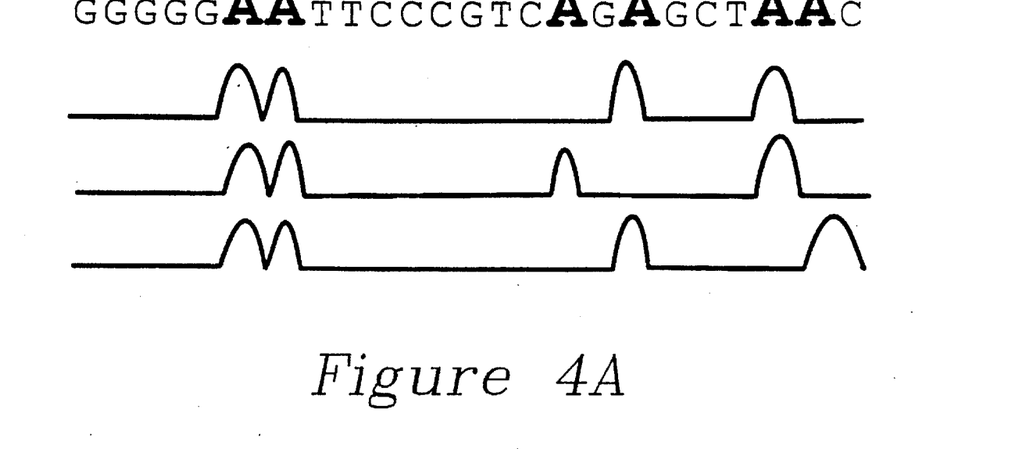
FIGS. 4A–D illustrate the compilation of scanning data to provide a complete nucleotide sequence.

An image of each aligned nucleic acid is obtained by applying a signal to the Y piezo-transducer 17, thereby moving the tip along a selected path. The error signal V from the feedback circuit corresponds to the height. An increased signal represents a labeled base. This signal is held in the processor's memory for each position along the path as a molecule is scanned. Data collection is initiated when the initiation marker is encountered, and completed when the path no longer contains detectable nucleic acid. A signal is then applied to the X piezo-transducer 14 to shift the tip to the next path. The path is then scanned and the signal is recorded. This is repeated until all the paths are scanned. FIG. 4A shows three scans of a molecule having labeled adenine bases, A. A plurality of scans are preferable in view of the fact that during the labeling of the polynucleotide all bases of the same kind are not labeled; therefore, multiple samples are required to assure that all the bases of a particular type are detected.

Figure 4B:
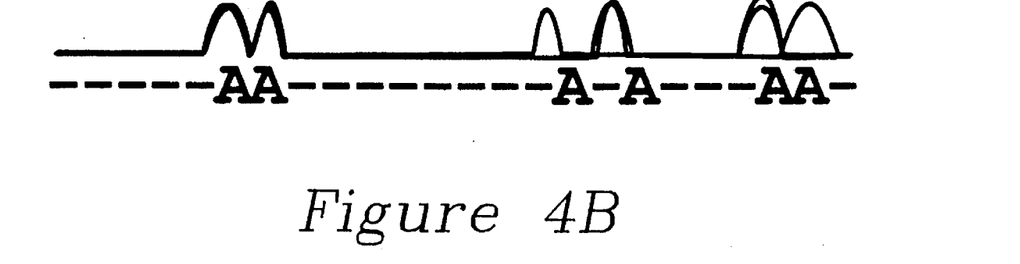
Figure 4C:
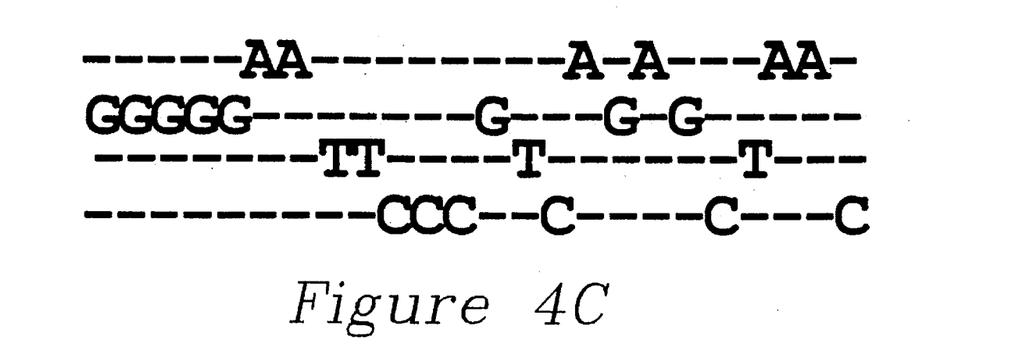
Figure 4D:
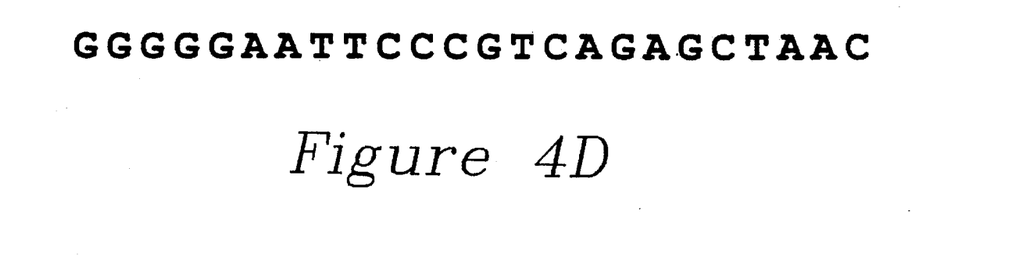

The processor compares the signals and provides a representation of all the tagged bases, FIG. 4B. In compiling the sequence for each base, only paths which are informative will be used. An informative path will generally start with an initiation marker, and preferably match a known sequence which immediately precedes or follows the initiation marker. Paths in which a loop is detected, either physically or by sequence comparison will be considered not informative. A consensus sequence for each base will be compiled. A path which differs from the consensus at more than about 25% of the positions will be considered not informative. As judged by the above criteria, only informative paths will be considered. The number of informative paths required for a complete data set, i.e. a data set in which 100% of the labeled bases are recorded, will depend on the efficiency of the labeling and alignment process. The number of paths required can be calculated statistically. A base sequence data set is compiled showing the position of each labeled base along the nucleic acid. The data sets from the four bases which comprise either DNA or RNA are then compiled as shown in FIG. 4C to provide a complete data set, showing the position of each of the four nucleotide bases in the nucleic acid molecule, FIG. 4D.

Figure 5A:
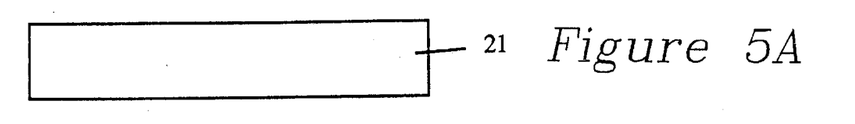
FIGS. 5A–H are cross-sections showing the substrate during fabrication for a silanol coating.
Figure 5B:
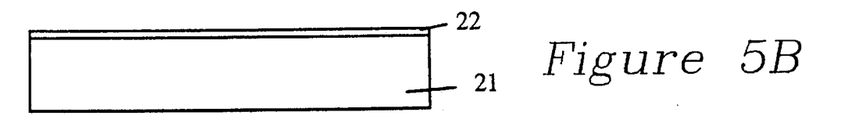
Figure 5C:
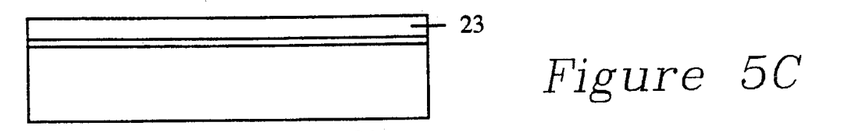
Figure 5D:
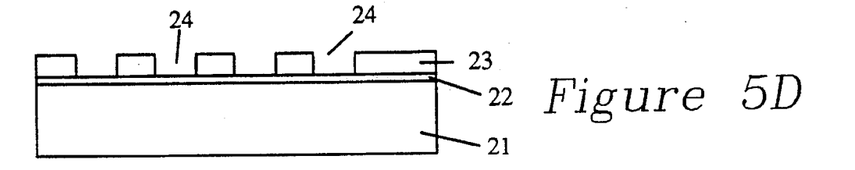
Figure 5E:
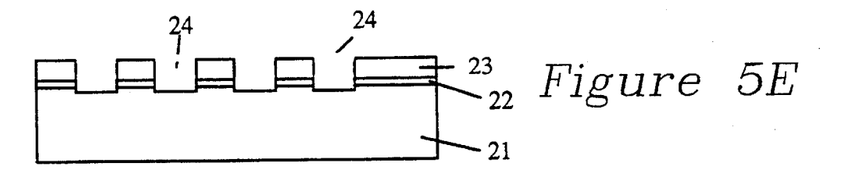
Figure 5F:
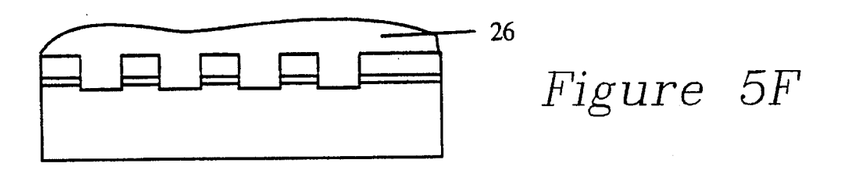
Figure 5G:
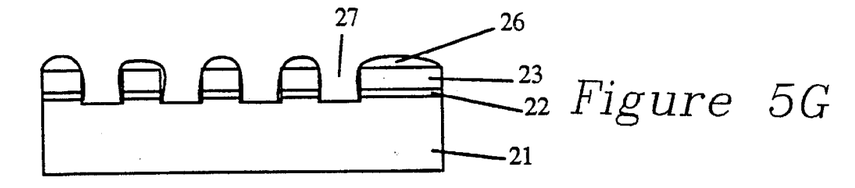
Figure 5H:
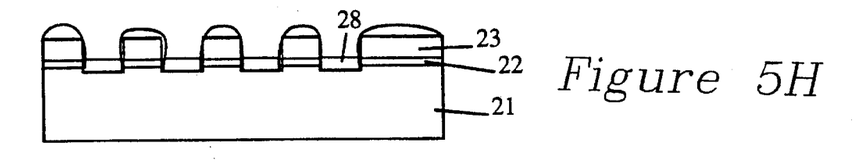

The fabrication of a substrate with trench alignment paths is illustrated in FIGS. 5A–5H. A silicon substrate 21, FIG. 5A, is provided with a thin, 100 Å nitride coating 22, FIG. 5B. A coating 23 of e-beam resist is applied by spinning the coating onto the surface of the silicon nitride film, FIG. 5C. A 500 Å line is developed using a low energy e-beam. The line is approximately 100 μm long, although any length suitable for retaining the molecule may be used. The resist is developed using readily available microelectronic photolithography techniques, e.g. direct write E-beam lithography, leaving a plurality of adjacent wenches 24, FIG. 5D. The substrate with resist mask is anisotropically etched to a depth of about 200 Å, removing the 100 Å of nitride and 100 Å of the underlying silicon 21, FIG. 5E. A nitride film 26 is deposited on the substrate to a thickness of 230 Å, FIG. 5F. The nitride is anisotropically etched, leaving a 50 Å-wide trench 27 with the silicon exposed at the bottom, FIG. 5G. The wafer is then placed in an oxidizing atmosphere and a 50 Å-thick coating of oxide 28 is grown onto the exposed silicon area, FIG. 5H. A shallower trench may be created by stripping nitride from the top after oxidation. The surface of the oxide is treated with a hydroxylated derivative of the base material, e.g. silanol with silicon, hydroxylated gallium with gallium arsenide, etc. The surface is then treated with a highly polar compound, such as 3-aminopropyltriethoxysilane, to form a nucleotide binding surface, as described with reference to FIGS. 2A and 2B.

Figure 6A:
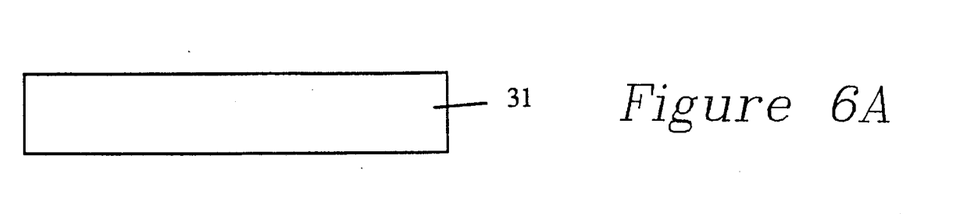
FIGS. 6A–F are cross-sections showing the substrate during fabrication for a gold coating.
Figure 6B:
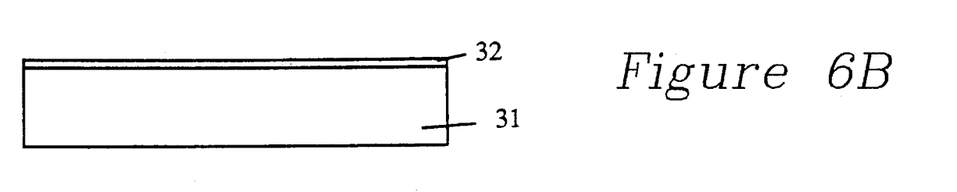
Figure 6C:
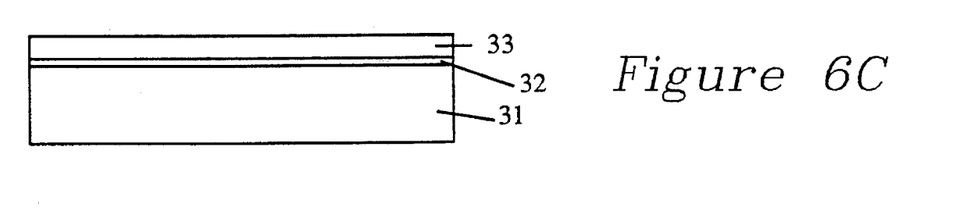
Figure 6D:
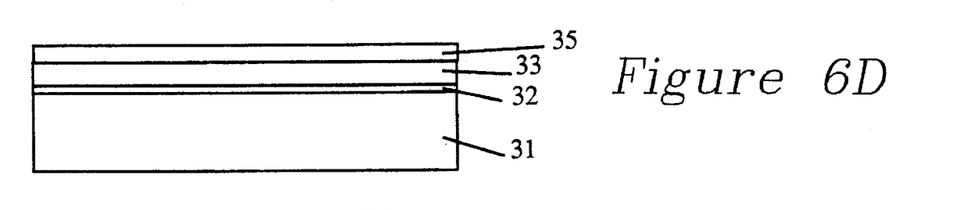
Figure 6E:
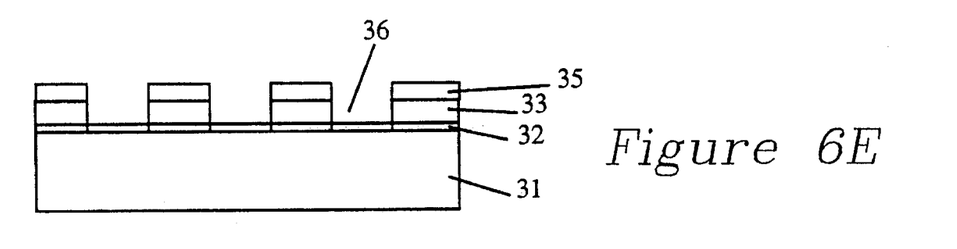
Figure 6F:
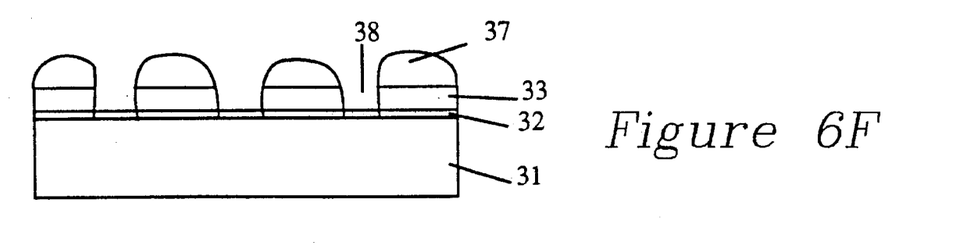

When the nucleic acid molecule is to be electrostatically bound, then the alignment paths will have a conductive layer at the base of the trench. FIGS. 6A–6F show the steps of a process for forming trenches with a gold base. A silicon wafer 31, FIG. 6A, is provided with a gold layer 32, which is approximately 750 Å thick, FIG. 6B. A thin nitride film 33 is grown onto the layer, FIG. 6C; a coating of resist 35 is spun onto the nitride layer, FIG. 6D; a 500 Å line is developed using a low energy e-beam; the resist is developed using readily available microelectronic photolithography techniques; and the substrate is anisotropically etched stopping at the gold surface. The resist is then removed; a 230 Å nitride film 37 is deposited on the substrate, and the nitride is masked and etched, leaving a 500 Å-wide trench 38 with gold exposed on the bottom of the trench as shown in FIG. 6F. The polynucleotide is held in the groove by applying a voltage between the gold and polynucleotide and maintaining a positive polarized surface, causing the phosphate ions to adhere to the gold surface, providing a structure of the type as described with reference to FIGS. 2A and 2B. While gold has been discussed as a conductive surface, it shall be understood that other conductive materials, as previously described, may also be used.

Figure 7A:
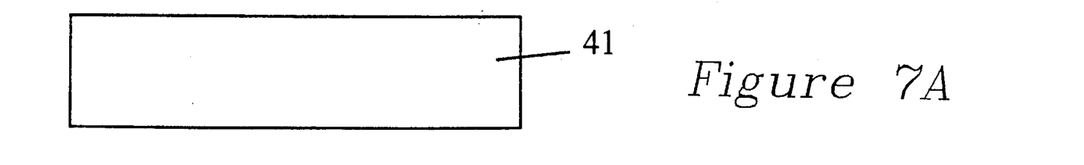
FIGS. 7A–E are cross-sections showing a raised path substrate during fabrication.
Figure 7B:
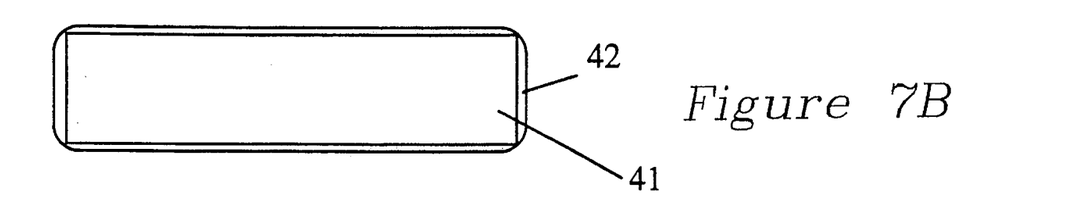
Figure 7C:
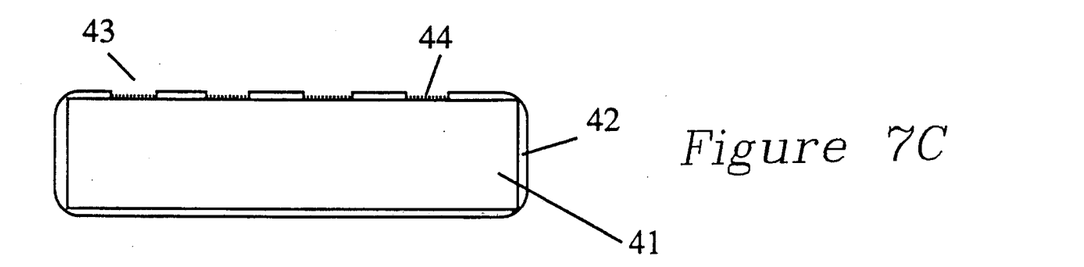
Figure 7D:
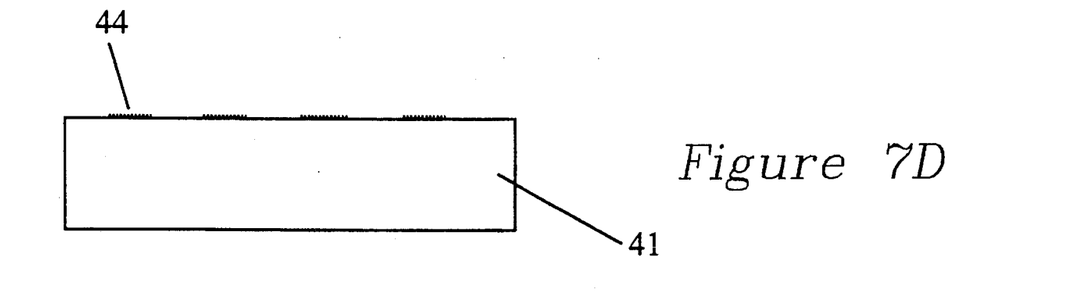
Figure 7E:
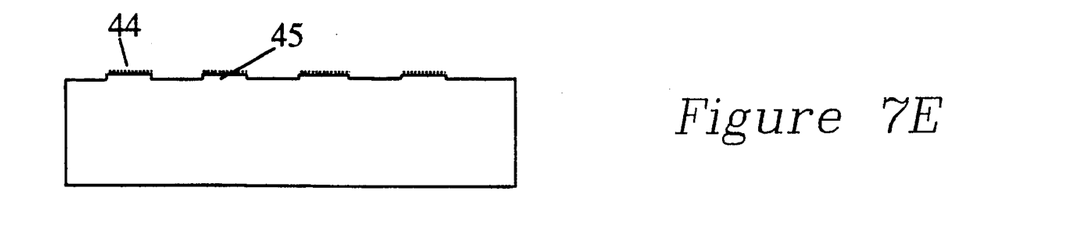

In FIGS. 7A–7E is shown a process for forming a flat or raised silicon path on the surface of a substrate, illustrated in FIGS. 3A and 3B. A silicon crystal base 41, FIG. 7A, is covered with a layer 42 of atomic hydrogen by dipping the substrate in a 10 percent hydrochloric acid solution, FIG. 7B. The substrate is then removed and dried by readily available microelectronic drying techniques. The hydrogen film is removed along paths 43 by the use of a scanning tunneling microscope, FIG. 7C. The current associated with the scanning tunneling microscope will simultaneously oxidize the silicon 44. The remaining hydrogen film is then removed, FIG. 7D. Optionally, the sample can then be dipped in hydrozene solution that will etch the silicon except for the areas covered by the oxide 44, FIG. 7E, thus generating plateaus 45 of at least about 5 Å with an oxide layer on top. The paths are usually at least about 5 Å wide and usually not more than about 50 Å wide. The height of the paths is usually not more than about 50 Å. The length of the path will usually be at least about 1 μm long, and may be about 100 or more μm long.

For all embodiments, the substrate may optionally include an initiation site, as shown in FIG. 8A–D. The initiation site will provide an initiation marker binding surface (IMBS), and will be positioned at one end of the alignment path. The initiation marker will be distinguishable by SXM, and may be a nucleic acid, protein, paramagnetic particle, etc. Preferably, the IBMS will differ from the DNA binding surface, e.g. a conductive DNA binding surface will be paired with a magnetic, or a polar IBMS; a polar DNA binding surface will be paired with a conductive, or a magnetic IMBS. The initiation site may be the width of the alignment path, or may be substantially wider, from about 1.0 nm to about 100 nm in width. In particular, a magnetic IMBS will require a larger initiation site to accomodate ferromagnetic particles, where the particles are from about 10 nm to about 100 nm in diameter.

Figure 8A:
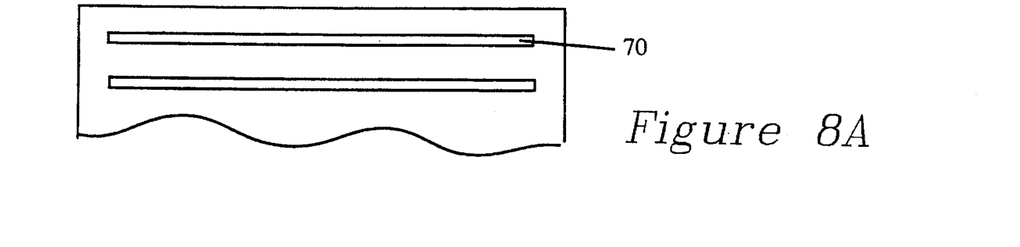
FIGS. 8A–E are a top view showing a substrate during fabrication of initiation sites.
Figure 8B:
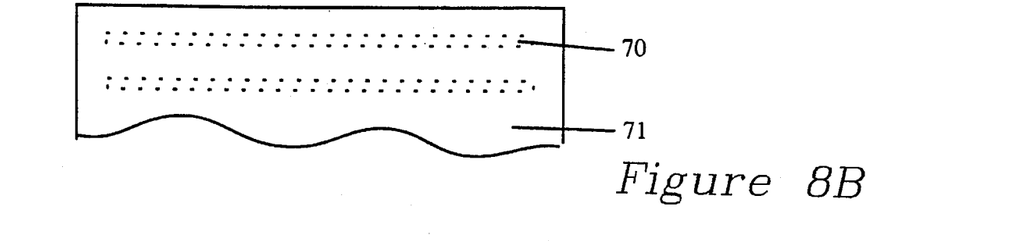
Figure 8C:
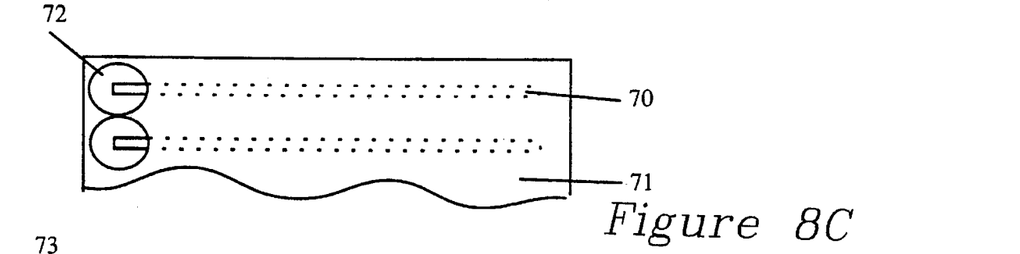
Figure 8D:
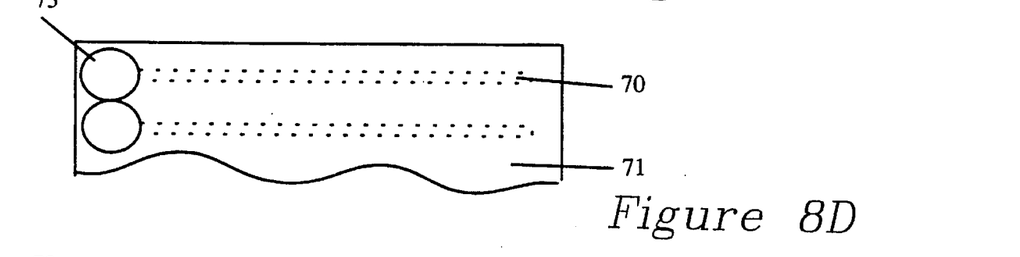
Figure 8E:
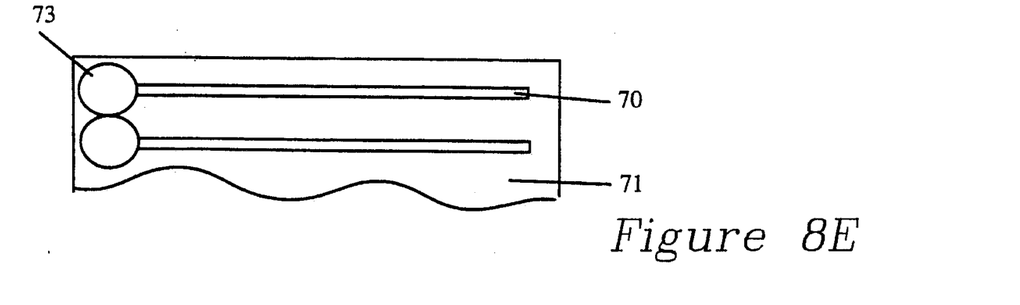

The substrate with initiation paths 70, FIG. 8A is coated with a resist 71, FIG. 8B. An opening 72 is developed at one end of each alignment path using readily available photolithography techniques, FIG. 8C. The opening 72 is etched, leaving a hole 73. The hole is plated with a conductive or ferromagnetic surface, or a coating of oxide is grown on the surface. The resist is then removed, FIG. 8E.

The DNA is prepared so that the sample contains a purified, linear molecular species, that is, substantially all of the DNA molecules in the sample will have the same sequence of nucleotides, or will be a mixture of a single stranded DNA and its complementary strand. A number of methods for generating purified DNA are known in the art. Of particular interest is the use of the polymerase chain reaction (PCR) to amplify the DNA which lies between two specific primers. The use of the polymerase chain reaction is described in Saiki, et al. (1985) Science 239:487. A review of current techniques may be found in Sambrook, et al. Molecular Cloning: A Laboratory Manual, CSH Press 1989, pp. 14.2–14.33. The use of PCR allows incorporation during DNA synthesis of base specific labels, and of labels which provide for an initiation marker. PCR can be used to amplify DNA up to about 35,000 nucleotides in length, usually DNA up to about 10,000 nucleotides in length (see J. Cohen [1994] *Science* 263:1564–1565). There is no theoretical limit to how small a fragment may be amplified, however in most cases the DNA will be at least about 18 nucleotides in length.

Use of PCR requires that there be a stretch of known sequence of at least about 12 nucleotides, more usually at least about 18 nucleotides, from at least one, and preferably both ends of the desired DNA molecule. The known sequence is used to generate the specific primers used for the amplification reaction. The reaction can proceed with a single primer, but in that case will not provide exponential amplification. For sequencing known genes in order to determine allelic or recombinational polymorphisms, it is convenient to chose primer sequence(s) from known conserved regions in the gene.

In sequencing DNA of unknown sequence one may ligate the unknown DNA to a DNA of known sequence in order to generate primer sites. For example, a fragment of DNA may be cloned into a number of commercially available vectors, many of which have defined insertion sites, and for which PCR amplification primers are sold. Most plasmid vectors can accomodate fragments of about 10,000 nucleotides or less, vectors based on lambda phage can accomodate fragments of up to about 24,000 nucleotides, and cosmids can accept 30,000 to 40,000 nucleotide inserts. Larger inserts can be cloned into artificial chromosomes, e.g. YACs.

Alternatively, amplification sites can be obtained by ligating oligonucleotide linkers having a known sequence to the desired DNA fragment. DNA fragments are obtained using any one of a variety of chemical and enzymatic cleavages, e.g. restriction endonucleases, single or double stranded DNAses, $^{32}$P scission, shear force, Fenton reagent, EtBr cleavage, etc. The fragment is then ligated to single or double stranded oligonucleotides with ligase, preferably T4 ligase. If the original fragment population contained a mixture of DNA species, then it is desirable to dilute the ligated fragments to an average of one molecule per PCR reaction before amplification, in order to amplify a single DNA species.

Samples containing a single DNA species can also be prepared by conventional methods, e.g. cloning into vector, preferably a high copy number plasmid or phage, and/or isolation of the DNA by density gradient, size fractionation, e.g. sucrose gradient, gel electrophoresis, affinity chromatography, molecular exclusion chromatography, etc. In order to have a sample containing linear molecules with defined ends, the DNA will usually be cleaved with a restriction endonuclease before the final purification step.

RNA may also be sequenced by the subject methods. It is most convenient, however, to convert the RNA into cDNA before sequencing, using conventional methods of oligo dT, hexamer priming, etc., and reverse transcriptase synthesis. If the RNA molecule itself is to be sequenced, then it may be purified by affinity chromatography, size fractionation, etc. Where the methods for alignment, complementation labeling, and scanning refer to DNA, it should be understood that RNA may also be used.

The DNA is made single stranded before scanning. It is denatured by any convenient means, such as heating to >95° C., treatment with NaOH, etc. The denatured DNA may be applied directly to the substrate, in which case both strands will be scanned. In a preferred embodiment, the complementary strands will be separated by strand separation gel electrophoresis, affinity chromatography, etc. and one of the complementary strands will be scanned.

If the DNA sample has been prepared by PCR, affinity chromatography provides a convenient method for strand separation. One of the amplification primers is end labeled with a group having a convenient reciprocal binding member, i.e. biotin, digoxigenin, fluorescein isothiocyanate (FITC), coumarin, etc. Such labeling methods are well known in the art, and can be performed with commercially available kits. In this way, one strand of the amplified DNA will have a label. After denaturation, the DNA is applied to an immobilized specific binding member for the end label, e.g. avidin or streptavidin for biotin, specific antibodies, etc., immobilized on a column, beads, microtiter plate, etc. The labeled DNA will bind to the immobilized binding member, and the unbound DNA is washed away. The bound DNA is eluted by any convenient means, such as a competitor molecule, e.g. free label, free binding member, etc.; with an increased ionic strength buffer, etc.

An initiation marker is not required for the practice of the invention, but it is convenient in providing a starting point for data analysis. An initiation marker is any group which is attached to the DNA, and which is distinguishable by SXM, as previously described. The initiation marker may be attached to the DNA prior to the DNA being bound to the alignment substrate, or may be present on the substrate before the DNA is added. Suitable initiation markers are proteins, e.g. DNA binding proteins such as helix-turn-helix specific DNA binding proteins and zinc finger specific binding proteins; DNA binding transcription factors, restriction endonucleases having an inactivated cleavage function; proteins which specifically bind labeled DNA, such as avidin and streptavidin to biotinylated DNA, antibodies to haptenated DNA, e.g. DNA conjugated to digoxigenin, FITC, coumarin, etc.; oligonucleotides which will specifically hybridize to a portion of the DNA, particularly oligonucleotides with chemically modified bases; or direct detection of end-labeled DNA. The binding group may conveniently be conjugated to a superparamagnetic particle, as described is U.S. Pat. No. 4,452,773, where the particle provides a large topographic marker of about 10–100 nm diameter.

If PCR has been used to generate the DNA sample, then the known primer sequence may be conjugated to the initiation marker. Preferably the inition marker will be used to end-label the amplification primer. During the final compilation of the sequence, the sequence of the amplification primer will be used to verify that a scan is informative.

When the DNA is linearly aligned on the substrate it may be useful, particularly with large fragments, to anchor one end of the DNA to one end of the alignment path. This is conveniently accomplished by using a substrate having an initiation marker binding site, and using the initiation marker as an anchor. The initiation marker may be bound to the substrate by one of several methods. A marker conjugated to a superparamagnetic particle may be bound to a ferromagnetic initiation site. A DNA or protein marker may be bound to the initiation site through electrostatic interaction with a polar coating, or to a conductive surface by application of a positive potential.

For sequencing, the DNA will be labeled with a base-specific marker that is distinguishable by SXM either by size (topography) or by conductivity, as previously discussed. In general, for reading one strand, four samples will be prepared, each corresponding to a different labeled base species. If both strands of a DNA will be scanned, then it is sufficient to label only two of the bases species, either both purines or both pyrimidines, where the complementary strand will provide the missing information. The base-specific label can be provided by one of two general techniques: synthetic labeling and complementation labeling.

Synthetic labeling exchanges one of the normal base species for a chemically altered analog during synthesis of the DNA. The method is appropriate when the DNA will be synthesized in vitro, particularly in combination with PCR. Because the label is incorporated during synthesis, it must be tolerated by the DNA polymerase. Generally the label will be less than about 1 kd, usually less than about 0.5 kd. Polymerases which lack proofreading functions are generally more tolerant of substituents, e.g. Klenow fragment, Taq polymerase, etc. In order to amplify long stretches of DNA, however, it may be necessary to use a mixture of polymerases, where at least one polymerase has a proof-reading function.

The purity, and efficiency of incorporation of the base analog will determine the percent of bases which will be labeled. In the final synthesized DNA product, usually at least about 10% of the targeted base, i.e. adenine for adenine derivatives, etc., will be labeled, more usually at least about 25%, preferably at least about 50%, and may be as high as 90%. The percent of labeled bases can be determined by various physical and enzymatic parameters. For example, a number of substituents are also fluorochromes, i.e. FITC, coumarin, etc., and the density can be calculated by fluorimetry. As discussed previously, the efficiency of labeling will determine the number of scans which must be performed.

Labeling by complementation relies on specific base pairing interactions. The label will be a free nucleotide or dinucleotide. It may be the naturally occurring base species, or an analog, preferably having a metal containing substituent group. It does not require a separate synthetic reaction, and can comprise substituents which are not tolerated by polymerases. The strength of the hydrogen bonding between bases is weaker than the covalent bonds used in synthetic labeling, and is an equilibrium reaction, so the conditions for scanning must be chosen to optimize pairing.

A single stranded DNA sample is combined with the complementation label in solution. The labeling may be performed while the DNA is aligned on a substrate, or prior to alignment. The hybridization conditions will maximize the interaction between base pairs, but will not allow non-specific pairing. Usually at least about 50% of the possible base pairs will be formed at a given time, more usually at least about 75% will be formed.

Suitable complementation labels include the four naturally occurring deoxyribonucleotides and ribonucleotides, and nucleotide analogs, including ferrocene conjugated nucleotides, hydroquinone/quinone, nitronyl, nitroxide, porphyrins, psoralens, coumarin, etc. Dinucleotides may be used to increase the strength of the bonding, using natural nucleotides or analogs. The use of dinucleotides will require that 16 sets of scans be performed, in order to account for all possible dinucleotides.

The labeled single stranded DNA will be aligned on the substrate for scanning. The substrate may have an initiation marker already bound, or the DNA and initiation marker may be added simultaneously. If the initiation marker is a large species, i.e. a protein or ferromagnetic particle, then it is preferable to bind the initiation marker to the substrate prior to adding the DNA. After alignment, the distance that the DNA will extend along the alignment path will be proportional to the number of base pairs of DNA. Usually the DNA will extend not more than about 10 µm, more usually the DNA will extend not more than about 5 µm, and may only extend about 100 to 1000 nm.

The DNA will be applied to the substrate for alignment in a dilute solution. It has been found that at concentrations greater than 100 µg/ml, aggregates predominate. Generally the DNA concentration will be greater than about 0.1 nM and not more than about 1 µM. The optimum concentration may be determined by titration, followed by scanning for the presence of isolated molecules. Conveniently, an aqueous solution will be used, although various other solvents, e.g. alcohols, ethers, toluene, benzene, ammonia, alkanes, etc. may find use. The salt and buffer composition will vary depending on whether the scan will be performed in a wet or a dry cell. A phosphate buffer is preferred in a wet cell when current will be applied, as most other common buffer salts are easily oxidized. The phosphate buffer will be usually at least about 0.5 mM $NaPO_4$, more usually at least about 1 mM $NaPO_4$, and usually not more than about 50 mM $NaPO_4$. When a dry cell scan is to be performed, low salt solutions are used, in order to minimize salt crystals forming after drying. Usually at least about 0.1 mM NaCl or other suitable salt, i.e. KCl, $MgCl_2$, $CaCl_2$, etc., more usually at least about 1 mM, and not more than about 50 mM, more usually not more than about 10 mM salt, will be used.

The substrate will be immersed in the DNA solution for at least about 10 minutes, usually at least about 1 hour, and may be immersed for as long as one day, or longer. The solution may be gently circulated, by rocking, rotation, etc. In one preferred embodiment, after the DNA is bound to the initiation marker, the solution is circulated directionally by peristaltic pump, etc., moving from the position of the anchor molecule and following the alignment paths across the substrate.

The DNA is then bound to the substrate surface. In a dry cell scan, the substrate will be removed from the DNA solution, optionally washed with a DNA-free solution, and allowed to dry. In a wet cell scan, the DNA will generally be bound by applying current to the solution, usually at least about +10 mV, more usually at least about +100 mV, and usually not more than about +250 mV. The current will usually be applied for at least about 10 minutes, and usually for not more than about 60 minutes. The DNA will remain adhered in the absence of a positive voltage potential, and the substrate may be rinsed in DNA-free solution after adherence.

The scanning tunneling microscope is used to characterize and quantify topographic and electronic changes along the length of the DNA. The sample will generally be scanned in constant current scanning mode (height imaging mode). Tunneling conditions will usually employ a current of from about 1 to 5 nM and a voltage of from about 20 to 300 mV, where the polarity of the voltage may be changed to characterize different substrates. Generally a sharp metallic tip of about 0.1 to 0.25 mm diameter is used. The line scan frequency will typically have about a 9 to 30 Hz range, where the time for one scan of 400 lines takes from 20 to 60 seconds. The output image is a gray scale or color 3 dimensional image of vertical changes. The vertical gray/color output bar will indicate the height variation in the DNA topography. The labeled bases will have a measurably higher output than the non-labeled bases. The output image will be used to compile a sequence for the scanned DNA.

The data set for each scan is compiled, and compared with the duplicate scans. In a preferred embodiment, the initiation marker is associated with a stretch of known sequence, which is used to align the data sets. A complete data set is compiled for each label: four sets when each base is labeled; two sets when only the purines or pyrimidines are labeled; and 16 sets when dinucleotides are used as labels. A complete nucleotide sequence is compiled from the combination of data sets.

The subject method is useful for any DNA sequencing. It is particularly appropriate for high throughput sequencing, such as that which is required for genome sequencing projects. It is also useful for the determination of DNA sequences in laboratory work where DNA constructions, cDNA cloning, chromosomal walking, polymorphisms, mutations, recombinations, etc., are analyzed to verify structures or to determine new sequences. In clinical practice, the subject method is used in determining the presence or absence of genetic polymorphisms of medical significance, e.g. cystic fibrosis; dystrophin mutations; hemoglobinapathies such as sickle cell, thalassemias, etc.; fragile X, Tay-sachs gene, etc. particularly for prenatal screening and genetic counseling. The following examples are offered by way of illustration and not by way of limitation.

EXPERIMENTAL

Sequencying Synthetically Labeled DNA in a Liquid STM Cell

1. Preparation of DNA.

The plasmid pBR322 is used as a test sequence. Throughout the procedures, ultrapure reagents and double-distilled water are used. The following 4 reactions are set up for amplification by the polymerase chain reaction, each having a deoxynucleotide replaced with its biotin-labeled analog (bio-dU, bio-dC, bio-dA and bio-dG, Boehringer Mannheim).

T labeling 1 ng pBR322 DNA (Promega, Madison, WI)
200 µM @ dCTP, dATP, dGTP
20 µM bio-dU
1 X PCR buffer (50 mM Tris-HCL, 50 mM NaCl, 10 mM MgCl$_2$)
10 U Taq Polymerase (Cetus)
10 ng pBR322 EcoRI primer -
GTATCACACGAGGCCCTT (SEQ ID NO:1)
(clockwise) (Promega), end labeled with digoxigenin using a reagent kit from Boehringer Mannheim, according to the manufacturer's direction.
10 ng pBR322 BamHI primer -
ATGCGTCCGGCGTAGA (SEQ ID NO:2)
(counterclockwise) (Promega)

C labeling 1 ng pBR322 DNA (Promega, Madison, WI)
200 µM @ dTTP, dATP, dGTP
20 µM bio-dC
1 X PCR buffer (50 mM Tris-HCL, 50 mM NaCl, 10 mM MgCl$_2$)
10 U Taq Polymerase (Cetus)
10 ng pBR322 EcoRI primer -
GTATCACACGAGGCCCTT (SEQ ID NO:1)
(clockwise) (Promega), end labeled with digoxigenin using a reagent kit from Boehringer Mannheim, according to the manufacturer's direction.
10 ng pBR322 BamHI primer -
ATGCGTCCGGCGTAGA (SEQ ID NO:2)
(counterclockwise) (Promega)

G labeling 1 ng pBR322 DNA (Promega, Madison, WI)
200 µM @ dCTP, dATP, dGTP
20 µM bio-dG
1 X PCR buffer (50 mM Tris-HCL, 50 mM NaCl, 10 mM MgCl$_2$)
10 U Taq Polymerase (Cetus)
10 ng pBR322 EcoRI primer -
GTATCACACGAGGCCCTT (SEQ ID NO:1)
(clockwise) (Promega), end labeled with digoxigenin using a reagent kit from Boehringer Mannheim, according to the manufacturer's direction.
10 ng pBR322 BamHI primer -
ATGCGTCCGGCGTAGA (SEQ ID NO:2)
(counterclockwise) (Promega)

A labeling 1 ng pBR322 DNA (Promega, Madison, WI)
200 µM @ dCTP, dTTP, dGTP
20 µM bio-dA
1 X PCR buffer (50 mM Tris-HCL, 50 mM NaCl, 10 mM MgCl$_2$)
10 U Taq Polymerase (Cetus)
10 ng pBR322 EcoRI primer -
GTATCACACGAGGCCCTT (SEQ ID NO:1)
(clockwise) (Promega), end labeled with digoxigenin using a reagent kit from Boehringer Mannheim, according to the manufacturer's direction.
10 ng pBR322 BamHI primer -
ATGCGTCCGGCGTAGA (SEQ ID NO:2)
(counterclockwise) (Promega)

The reaction is subjected to 30 cycles of amplification. A 375 bp fragment is amplified, having one strand end-labeled with digoxigenin. In each reaction, one of the nucleotides is substituted with a biotin-labeled analog.

The reaction mix is extracted with phenol:chloroform several times, and ethanol precipitated. The amplified DNA is resuspended in 1 X binding buffer, heated to 100° for several minutes to denature, and quenched on ice. The denatured DNA is applied to an affinity column of sepharase conjugated anti-digoxigenin monoclonal antibody (Boehringer Mannheim). The clockwise strand, having the digoxigenin labeled primer incorporated, is bound to the column. The unbound DNA is washed free of the column. The bound strand is eluted with a 100 mM solution of free digoxigenin, and collected. The single strand is ethanol precipitated, washed with 70% ethanol, and resuspended in TE (10 mM Tris, 1 mM EDTA).

2. Formation of alignment substrate with oxide binding surface:

A silicon wafer (crystal orientation 111) is oxidized in a furnace at 900° C., forming an oxide layer 200 Å thick. The oxide film is stripped off with a solution of HF, leaving clean smooth silicon. 100 Å of LPCVD nitride is deposited on the wafer at 800° C. 1000 Å of e-beam resist is spun onto the wafer. A line pattern with 500 Å wide lines, 100 µm long are written with direct write e-beam on the resist. Exposed lines are developed with conventional e-beam resist techniques. Nitride film with resist mask is etched in a very low pressure etcher (<2 mtorr) with $CF_4$, allowing selectivity between the nitride and silicon surface. The photo resist layer is stripped off, and the wafer cleaned in HF. 230 Å of LPCVD nitride is deposited on the etched wafer. The wafer is placed in a low pressure etcher, and etched with CF4 to remove 120 Å of nitride. The wafer is placed in an oxidation furnace, and 50 Å of thermal oxide grown at 850° C. The wafer is washed in a solution of silanol, followed by a wash in 3-aminopropyltriethoxysilane.

3. Formation of alignment substrate with conductive binding surface:

A silicon wafer (crystal orientation 111) is oxidized in a furnace at 900° C., forming an oxide layer 200 Å thick. The oxide film is stripped off with a solution of HF, leaving clean smooth silicon. A metal film of at least 200 Å is deposited on the silicon surface. 100 Å plasma CVD nitride is deposited at 400° C. 1000 Å of e-beam resist is spun on the wafer. A line pattern with 500 Å wide lines, 100 µm long are written with direct write e-beam on the resist. Exposed lines are developed with conventional e-beam resist techniques. Nitride film with resist mask is etched in a very low pressure etcher (<2 mtorr) with $CF_4$, allowing selectivity between the nitride and silicon surface. The photo resist layer is stripped off, and the wafer cleaned in HF. 230 Å of plasma CVD nitride is deposited on the surface. The wafer is placed in a low pressure etcher and etched with $CF_4$ to remove 120 Å of the nitride.

4. Binding DNA to substrate:

The amplified DNA fragment is resuspended in PBS at a concentration of 1 µg/ml. The substrate is placed in a chamber flooded with the DNA solution, having a peristaltic pump maintaining a current flow across the substrate, starting at the antibody dipped end. Flow is left on for one hour.

5. Anchoring DNA to the substrate

The DNA solution is rinsed from the substrate. The substrate is placed in an electrolysis cell, and a current of 100 mV applied for 20 minutes.

6. Reading the sequence:

The substrate is scanned in constant current scanning mode (height imaging mode), using a current of 1 to 5 nM and a voltage of from about 20 to 300 mV. The line scan frequency is in the 9 to 30 Hz range, where the time for one scan of 400 lines takes from 20 to 60 seconds.

The vertical output bar indicates the height variation in the DNA topography. The labeled bases have a measurably higher output than the non-labeled bases. The output image is used to compile a sequence for the scanned DNA.

The data set for each scan is compiled, and compared with the duplicate scans. The amplification sequence GTATCACACGAGGCCCTT (SEQ ID NO:1) is used to align the data sets. A complete data set is compiled for each labeled base. A complete nucleotide sequence is compiled from the combination of data sets.

Sequencing Synthetically Labeled DNA in a Dry Cell

DNA is prepared as described in Example 1.

DNA is added to the substrate as previously described. The substrate is washed several times with a solution of 1 mM NaCl, and dried.

Use of an Initiation Marker as an Anchor

A substrate is prepared with a conductive DNA binding surface, and a ferromagnetic initiation marker binding surface. Prior to addition of the DNA, the substrate is submerged in a 1 µg/ml solution of superparamagnetic particles ranging in size from 10 to 100 mM, conjugated to anti-digoxigenin antibody (Miltenyi-Biotec GmBH). The particles are bound to the substrate in a magnetic field of 0.5 Tesla. The substrate is washed 4 times with buffer. The digoxigenin labeled DNA is added to the substrate as previously described, and allowed to bind to the antibody. During the scanning procedure, the iron oxide particle provides an extremely distinct peak, allowing alignment of the following sequence.

Sequencing Chromosomal DNA

Preparation of DNA

A suspension of $10^6$ normal human cells are suspended in 50 µl of 0.5% agarose, 50 mM NaCl, 10 mM Tris, pH 8.0. The agarose is allowed to harden to form an agarose plug. The plug is then submerged in 200 µl of a solution containing proteinase K and RNAse and incubated at room temperature overnight. The plug is then moved into 200 µl of a solution containing 200 U NotI, in 1X NotI buffer (Promega). The reaction mix is incubated overnight at 37° C. The solution is aspirated off, and the enzyme inactivated by heating at 65° for 10 minutes. The melted agarose is diluted in a 200 µl of buffer D (6 mM Tris, pH 8; 6 mM $MgCl_2$; 150 mM NaCl) with 0.1 µg NotI compatible linkers, 5' AGCGGCCGCTCGCCAGGGTTTTCCCAGTCACGAC (SEQ ID NO:3). The solution is allowed to cool, and. 10 U T4 ligase added. The ligation reaction is incubated at room temperature overnight.

The DNA is electrophoresed on a 0.8% agarose gel, and the high molecular weight fraction (>10 kb) excised and eluted. The eluted DNA is serially diluted in 1X PCR buffer to an average concentration of one molecule per tube. The polymerase chain amplification is performed as in example 2, using digoxigenin end labeled NotI linkers as amplification primers.

The DNA is aligned and scanned as described in example 1.

It is evident from the above results that the subject invention provides for an improved method of sequencing polynucleotides. The ease of labeling and aligning the nucleic acids for scanning and sequence determination allows for automation, so as to significantly increase the ability to sequence large amounts of DNA.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An apparatus for determining the sequence of a nucleic acid, comprising:

a fabricated substrate comprising at least one alignment path having a nucleic acid binding surface;

a scanning microscope for scanning along said alignment path to provide an output signal representative of the position of each labeled base in said nucleic acid sequence;

a data processor for processing the signal to provide an output signal representative of the sequence of said nucleic acid.

2. An apparatus according to claim 1, wherein said microscope is a scanning tunneling microscope.

3. An apparatus according to claim 1, wherein said substrate comprises a purality of alignment paths.

4. An apparatus according to claim 3, wherein said substrate further comprises an initiation site for each of said alignment paths.

5. A method for determining the nucleotide sequence of a DNA, the method comprising:

(1)(A) preparing purified, linear single-stranded DNA, wherein said DNA comprises a label distinguishable by scanning microscopy (SXM) specific for one base species;

(B) aligning said DNA on a fabricated substrate comprising at least one alignment path having a nucleic acid binding surface;

(C) scanning said aligned DNA by STM;

(D) recording the position of said label along said aligned DNA to provide a base sequence-data set;

(2) repeating steps (A) to (D) with a label specific for each nucleoside base; and (3) compiling each of said base sequence-data sets to provide a complete sequence data set, wherein said data set describes the position of each nucleotide in the sequence of said DNA.

6. A method according to claim 5, wherein said substrate comprises a plurality of alignment paths; wherein said scanning of aligned DNA is repeated for said plurality of alignment paths; and wherein said base sequence data set comprises a compilation of base sequence-data sets from said plurality of scans.

7. A method according to claim 6, wherein said purified, linear single stranded DNA is a mixture of complementary strands, and wherein said repeating steps (A) to (D) with a label specific for each nucleoside base is limited to one of purine specific labels or pyrimidine specific labels.

8. A method according to claim 6, wherein said purified, linear single-stranded DNA further comprises an initiation marker.

9. A method according to claim 6, wherein said preparing purified, linear single-stranded DNA comprises the steps of:
    amplifying said DNA by polymerase chain reaction in the presence of a nucleotide analog having a substituent group distinguishable by SXM.

10. A method according to claim 6, wherein said preparing purified, linear single-stranded DNA comprises the steps of:
    amplifying said DNA by polymerase chain reaction in the presence of a nucleotide analog having a substituent group distinguishable by SXM wherein at least one of the primers for said amplification comprises an initiation marker distinguishable by SXM.

11. An apparatus according to claim 1, wherein said nucleic acid binding surface is a conductive coating.

12. An apparatus according to claim 1, wherein said nucleic acid binding surface is a silanol coating.

13. An apparatus according to claim 1, wherein said alignment path is a trench of at least about 5 Å deep, at least about 20 Å wide and at least about 1 μm long.

14. An apparatus according to claim 1, wherein said alignment path is level with the surface of the substrate, and is at least about 5 Å wide and at least about 1 μm long.

15. An apparatus according to claim 1, wherein said alignment path is raised above the surface of the substrate at least about 5 Å, is at least about 5 Å wide and at least about 1 μm long.

16. An apparatus for determining the sequence of a nucleic acid, comprising:
    a fabricated substrate comprising at least one alignment path having a nucleic acid binding surface, wherein said substrate is formed from a base material selected from the group consisting of crystalline silicon, germanium, and III–V compounds, said base material having a root mean surface number of less than about 5 angstroms;
    a scanning microscope for scanning along said alignment path to provide an output signal representative of the position of each labeled base in said nucleic acid sequence;
    a data processor for processing the signal to provide an output signal representative of the sequence of said nucleic acid.

* * * * *